United States Patent [19]
Peet et al.

[11] Patent Number: 5,817,874
[45] Date of Patent: Oct. 6, 1998

[54] PROCESS FOR ALKYLATING AND SMILES REARRANGEMENT OF HYDROXY AROMATICS

[75] Inventors: Norton P. Peet; John J. Weidner, both of Cincinnati, Ohio

[73] Assignee: Hoechst Marion Roussel, Inc., Cincinnati, Ohio

[21] Appl. No.: 820,060

[22] Filed: Mar. 18, 1997

Related U.S. Application Data

[60] Provisional application No. 60/073,842 Mar. 21, 1996.
[51] Int. Cl.$^6$ .......................... C07C 233/06; C07C 231/08
[52] U.S. Cl. ........................ 564/222; 564/218; 552/286; 549/57
[58] Field of Search .................................. 564/218, 222; 552/286; 549/57

[56] References Cited

FOREIGN PATENT DOCUMENTS

B.1 0002309   6/1979   European Pat. Off. .

OTHER PUBLICATIONS

S. Ramsby et al., J. Med. Chem., 32:1198–1201 (1989).

Coutts, et al., J. Chem. Soc. Perkin Trans. 1 (1990) pp. 767–771.

R. Bayles, et al., Synthesis, 31:31–33, (1977).

R. Bayles, et al., Synthesis, 31:33–34, (1977).

*Primary Examiner*—Shailendra Kumar
*Attorney, Agent, or Firm*—T. Helen Payne

[57] ABSTRACT

The present invention is a process of converting a hydroxy aromatic into a 2-hydroxy-N-arylacetamide, comprising:

(1) treating a reaction mixture comprising a salt of a hydroxy aromatic with an alkylating agent; and (2) treating the reaction mixture with a Smiles solvent system and raising the temperature of the reaction mixture.

32 Claims, No Drawings

PROCESS FOR ALKYLATING AND SMILES REARRANGEMENT OF HYDROXY AROMATICS

This application claims the benefit of Provisional Ser. No. 60/073,842, filed Mar. 21, 1996.

BACKGROUND OF INVENTION

A Smiles rearrangement describes a pattern of reactions involving intramolecular nucleophilic aromatic substitution which results in the migration of one heteroatom to another on an aromatic ring. The Smiles rearrangement works with a variety of heteroatoms, including oxygen, sulfur and nitrogen. The Smiles rearrangement of phenols, including fused-ring heterocyclic phenols, into corresponding anilines is described by I. G. C. Coutts and M. R. Southcott in *J. Chem. Soc. Perkin Trans. I*, 1990;767–771. The syntheses described by Coutts and Southcott replace the hydroxy group on an aromatic ring, optionally fused into a larger ring system, with an amino group. The paper describes the synthesis as a distinct three-step process, with the purification of each intermediate. The first step is an alkylation of the alcohol into a 2-aryloxyacetamide. The second step is the actual Smiles rearrangement of the aryloxyacetamide into the 2-hydroxy-N-arylacetamide. Finally, the 2-hydroxy-N-arylacetamide is hydrolyzed into the corresponding aromatic amine. The known Smiles rearrangements of aromatic amides or amines from hydroxy aromatics involve purification of the 2-aryloxyacetamide intermediates.

Methods of direct conversion of phenols to anilines are known, but most have serious drawbacks. For example, transformations of 4-chloro-2-phenylquinazoline are limited to substrates resistant to high temperatures and basic conditions. Similarly, a method of converting phenols via diethyl phosphate esters requires the use of toxic diethyl chlorophosphate and of potassium in liquid ammonia. The Bucherer reaction is restricted to naphthalenes and related heterocycles. I. G. C. Coutts and M. R. Southcott *J. Chem. Soc. Perkin Trans. I*, 1990;767–771. Therefore, there is a need for a general synthesis of anilines from phenols which is applicable to a broad range of phenols, which doesn't require the use of toxic reagents, requires few steps and produces good yields.

Aromatic amines are of great interest in both the chemical and pharmaceutical industries. For example, phenacetin, an acetylated ethoxyaniline, is a known analgesic. Additionally, aromatic amines are useful intermediates for the preparation of more complicated organic molecules. Aromatic amines are used in the preparation of many commercially important dyestuffs, such as azine, azo and azoxy dyes. Conversion of 3-hydroxy estrogens into their corresponding amines is described by Coutts and M. R. Southcott, supra.

SUMMARY OF THE INVENTION

The present invention is an improved method of effecting an alkylation and Smiles rearrangement of a hydroxy aromatic to a 2-hydroxy-N-arylacetamide, where the alkylation and Smiles rearrangement are carried out without purifying the 2-aryloxyacetamide intermediate. The avoidance of the purification step is significant in terms of minimizing the time, cost and resources necessary during the synthesis of aromatic amines and yet obtains good overall yields.

The present invention is a process of converting a hydroxy aromatic into a 2-hydroxy-N-arylacetamide, comprising the steps of:

(1) treating a reaction mixture comprising a salt of a hydroxy aromatic with an alkylating agent; and (2) treating the reaction mixture with a Smiles solvent system and raising the temperature of the reaction mixture.

Another embodiment of the process comprises the steps of:

(1) treating a reaction mixture comprising an alkylating solvent system and the a hydroxy aromatic to form a salt;

(2) treating the reaction mixture with an alkylating agent; and (3) treating the reaction mixture with a Smiles solvent system and raising the temperature of the reaction mixture.

DETAILED DESCRIPTION OF THE INVENTION

The present invention is an improved process of effecting an alkylation and Smiles rearrangement of a hydroxy aromatic to an 2-hydroxy-N-arylacetamide, where the alkylation and Smiles rearrangement are carried out without purifying the 2-aryloxyacetamide intermediate. First, a salt of the hydroxy aromatic is formed in the presence of an alkylating solvent system, to which an alkylating agent is added. Finally, a Smiles solvent system is added to the reaction mixture containing the 2-aryloxyacetamide intermediate and the reaction mixture is heated to effect the Smiles rearrangement and form the 2-hydroxy-N-arylacetamide product. Optionally, the 2-hydroxy-N-arylacetamide is hydrolyzed to form the corresponding aromatic amine.

Suitable hydroxy aromatics for the present reaction are well known to those skilled in the art. Hydroxy aromatics are optionally substituted in the ortho, meta and para positions. Preferred ortho substituents include activating groups such as nitro, and alkoxy, methyl and ethyl groups. Preferred meta and para substituents include nitro, alkoxy, halogen, $C_{1-20}$ alkyl and $C_{1-10}$ alkoxy. Preferred hydroxy aromatics are compounds of the formula:

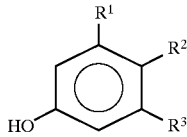

wherein $R^1$, $R^2$ and $R^3$ are each independently halogen, $C_{1-20}$ alkyl, $C^{1-10}$ alkoxy. Hydroxy aromatics may be simple hydroxy aromatics having a single aromatic ring, such as phenols and substituted alkoxyphenols. Preferred hydroxy aromatics are substituted at the meta and para positions. Complex hydroxy aromatics may also be used in the present invention, where $R^1$ and $R^2$ or $R^2$ and $R^3$ may be combined to formed multiple carbon fused ring structures of varying degrees of saturation, or where ring structures are attached as substituents. Suitable complex ring structures include fully aromatic complex ring structures such as indene, naphthalene, anthracine, phenanthrene, benzofuran and dibenzofuran, as well as their partially and fully saturated counterparts, such as dihydroindene, 1,2- and 2,3-dihydronaphthalenes, di-, tetra-, hexa- and octa-hydroanthracine, di-, tetra-, hexa- and octa-hydrophenanthrene, di- and tetra-hydrodibenzofuran. Preferred complex aromatic ring structures include steroids. Specific examples of suitable steroids for use in the invention include naturally occurring steroids and synthetic steroids. Especially preferred are estrogens, of which estradiol, estrone, 6-,7-, 8-, 9-, 11-, 14-, 15-dehydroestrone, equilenin and cyclopentaphenanthrene are particularly preferred. Preferred synthetic steroid mimics are triarylethylenes and tamoxifen analogs are particularly preferred. In complex ring structures, the carbon atoms in the rings other than the those in the hydroxy aromatic ring are optionally substituted with a wide variety of substituents known to those in the art, including $NH_2$, $NO_2$, SH, $SO_3H$, $CO_2H$, CN, halogens, thioethers, alkyl, alkoxy groups and other functional groups such as carbamates, ethers, amides, and esters.

The salt of the hydroxy aromatic compound may be formed according to methods well-known in the art. Preferably, the salt of the hydroxy heteroaromatic compound is formed in the presence of an alkylating solvent system, to which an alkylating agent is added.

The alkylating agent serves as a donor of a substituent capable of undergoing intramolecular nucleophilic substitution, or the Smiles rearrangement. Alkylating agents useful in the present invention are well known to those of ordinary skill in the art. Generally, suitable alkylating agents are comprised of an amide and halogen functional group separated by two carbon atoms of the following general formula:

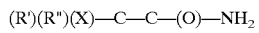

(R')(R")(X)—C—C—(O)—NH$_2$ wherein X is a leaving group. Suitable leaving groups include halogens and OR, where R isp-toluenesulfonyl or methylsulfonyl. A preferred leaving group is selected from bromine, chlorine and iodine. An especially preferred leaving group is bromine.

R' and R" of the alkylating agent are independently H or $C_{1-6}$alkyl, straight or branched chain. Only one of R' or R" may be hydrogen. It is preferred that when one of R' or R" is hydrogen, the other is a larger alkyl such as isopropyl, sec-butyl or tert-butyl or equivalent pentyl or hexyl groups. It is especially preferred that when one of R' or R" is hydrogen, the other is tert-butyl. $C_{1-6}$ alkyl is a straight and branched one to six carbon group including methyl, ethyl, propyl, isopropyl, n-butyl, sec-butyl, tert-butyl, pentyl and hexyl.

A preferred alkylating agent is where X is a halogen and R' and R" is $C_{1-4}$ alkyl. An especially preferred alkylating agent is where X is bromine and at least one of R' and R" is methyl or ethyl. Preferred alkylating agents are secondary haloalkylamides and, most preferred are tertiary haloalkylamides, with 2-bromo-2-methylpropanamide and 2-bromo-2-ethylbutanamide being especially preferred.

Alkylating solvent system generally comprises a strong base, an ethereal solvent and a large alkaline metal cation.

A strong base is capable of extracting the alcoholic proton of the hydroxy aromatic. A single strong base may be used, or a combination of two or more strong bases may be used. Suitable strong bases include sodium hydride, potassium hydride, lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium, and mixtures thereof. The hydride bases are preferred, such as sodium hydride, lithium hydride, potassium hydride and mixtures thereof. Sodium hydride is especially preferred.

An ethereal solvent is used to solvate the reaction components, including the alkylating agent and large alkaline metal cation. The ethereal solvent should be polar and non-nucleophilic. Suitable ethereal solvents include 1,4-dioxane, 1,3-dioxane, tetrahydrofuran (THF), dimethoxyethane (DME), 2-methoxyethyl ether, propyl ether, isopropyl ether, n-butyl ether, sec-butyl ether, tert-butyl ether, n-butylmethyl ether, tert-butylmethyl ether, n-butylethyl ether, sec-butylethyl ether, tert-butylethyl ether, n-butylpropyl ether, sec-butylpropyl ether, tert-butylpropyl ether and mixtures thereof. Preferred ethereal solvents have relatively low boiling points. 1,4-Dioxane and 1,3-dioxane are preferred. 1,4-Dioxane is especially preferred.

A large alkaline metal cation is believed to function as an electron transfer facilitator. More specifically, the large metal cation is thought to promote radical alkylation reactions. Inorganic cesium compounds are preferred. Suitable examples of sources of large alkaline metal cations include cesium carbonate ($Cs_2CO_3$), cesium acetate ($CsCO_2CH_3$), cesium bicarbonate ($CsHCO_3$), cesium bromide (CsBr), cesium chloride (CsCI), cesium fluoride (CsF), cesium iodide (CsI). Cesium carbonate is preferred.

A Smiles solvent system is added to the reaction mixture to promote the Smiles rearrangement. The Smiles solvent system is designed to solvate the reagents, act as an anion-coordinating agent by promoting and/or stabilizing the anionic form of the 2-aryloxyacetamide intermediate and to coordinate or make the 2-aryloxyacetamide intermediate a stronger nucleophile, through conversion into an anion, and thus facilitating a Smiles rearrangement.

A Smiles solvent system comprises an amide solvent, an anion-coordinating agent and a strong base. Preferably, there are at least molar equivalents of the anion-coordinating agent to alkaline metal cation.

The Smiles solvent system may be premixed or each component added sequentially to the reaction mixture in any order.

A strong base is capable of extracting the amide proton of the 2-aryloxyacetamide intermediate. A single strong base or a combination of two or more strong bases may be used in the present invention. Suitable strong bases include sodium hydride, potassium hydride, lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium or mixtures thereof. The hydride bases are preferred, such as sodium hydride, lithium hydride and potassium hydride. Sodium hydride is especially preferred. The strong base may be the same strong base used as the strong base for alkylation.

The amide solvent is preferably 1-methyl-2-pyrrolidinone (NMP), dimethylformamide (DMF), dimethylacetamide (DMA) or mixtures thereof. NMP is preferred amide solvent.

The anion-coordinating agent may be N,N'-dimethyl-N,N'-propyleneurea; also known as 1,3-dimethyltetrahydropyrimidin-2(1H)-one (DMPU) or hexamethylphosphoric triamide (HMPA) or a combination thereof. DMPU is the preferred anion-coordinating agent.

The volume ratio of a amide solvent to a anion-coordinating agent is optionally from about 1:1 to about 40:1. Preferably, the ratio of amide solvent to anion-coordinating agent is from about 5:1 to about 15:1. The ratio of amide solvent to anion-coordinating agent is especially preferred to be between about 7:1 to about 12:1. The most preferred ratio of amide solvent to anion-coordinating agent is about 10:1.

The salt of the hydroxy aromatic is formed by reacting a hydroxy aromatic in the presence of an alkylating solvent system. The reaction mixture is optionally stirred for a period sufficient to form a salt of the hydroxy aromatic. Preferably, when sodium hydride is used in the alkylating solvent system, evolution of hydrogen gas continues until the formation of the hydroxy aromatic salt is substantially complete. Preferably, the reaction mixture is heated during the formation of the salt. Higher temperatures generally require shorter reaction time for the formation of the salt and lower temperatures generally requires longer reaction time.

An alkylating agent is preferably added to the reaction mixture after formation of the hydroxy aromatic salt. In a more preferred embodiment, the reaction mixture is stirred at reflux until substantial completion of the alkylation occurs. Reaction progress of the alkylation may be monitored by known techniques, including thin-layer chromatography (TLC), gas chromatography (GC) or high performance liquid chromatography (HPLC). TLC is preferred. After alkylation, a Smiles solvent system, preferably a combination of amide solvent, anion-coordinating agent and strong base, is added to the reaction mixture.

The temperature of the reaction mixture is raised to a temperature sufficient to effect the Smiles rearrangement. Faster reaction time is expected with higher temperatures and longer reaction time is expected with lower temperatures. Preferred reaction temperature is between about 65° C. to about 250° C., preferably between about 125° C. to 200° C. A more preferred reaction temperature is between about 125° C. to about 175° C. The most preferred reaction temperature is about 150° C. The reaction mixture is optionally stirred during the Smiles rearrangement.

Reaction progress of the Smiles rearrangement is optionally monitored by any known technique, for example, thin-layer chromatography (TLC), gas chromatography (GC), high performance liquid chromatography (HPLC). TLC is preferred. Upon completion of the Smiles rearrangement, the 2-hydroxy-N-arylacetamide product is purified by known methods.

Optionally, the acylated aromatic may be hydrolyzed under known conditions to give the corresponding aromatic amine.

EXAMPLE 1

Preparation of 2-Bromo-2-methyl propanamide

To a 1 L Erlenmeyer was added bromoisobutyryl bromide (Aldrich, 23.0 mL, 42.0 g, 0.18 mole) and hexane (500 mL). The mixture was vigorously stirred at 0° C. and concentrated aqueous $NH_4OH$ (EM Scientific, 80 mL) was added in portions over 30 min. The resulting mixture was stirred an additional 30 min. at 0° C., then the white precipitate was filtered by suction and washed several times with ice water. After drying on the funnel about 1 h, the crude product (41.7 g, 0.25 mole, 140% crude yield) was recrystallized from 200 mL $CHCl_3$ and 20 mL hexane. Product was obtained as shiny white plates (31.2 g, 0.18 mole, 100%): mp 146–148° C.

EXAMPLE 2

Preparation of N-(3-amino-1,3,5,(10)-estratrien-17-one-yl)-2-hydroxy-2-methylpropionamide To a solution of estrone (1.00 g, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl -propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), to obtain N-(3-amino-1,3,5,(10)-estratrien-17-one-yl)-2-hydroxy-2-methylpropionamide as an off-white solid (770 mg, 2.17 mmol, 58.6% yield). mp 159–160° C. $^1$H NMR (400 MHz, $CDCl_3$) δ 8.60 (br s, 1H, N—H), 7.44 (d, 1H, $C_4$—H, J=1.99 Hz), 7.27–7.21(om's, 2H, $C_1$—H and $C_2$—H), 2.90 (dd, 2H, $C_6$—H, J=9.11, 4.27 Hz), 2.56–1.93 (om's, 8H), 1.70–1.40 (om's, 6H), 1.54 (s, 6H, $C(CH_3)_2$), 0.90 (s, 3H,$C_{18}$–$CH_3$); $^{13}$CNMR(100 MHz, $CDCl_3$)δ 221.0, 174.1, 137.3, 135.9, 135.3, 125.8, 199.9, 117.1, 74.2, 50.4, 48.0, 44.1, 38.2, 35.8, 31.5, 29.5, 27.9, 26.4, 25.7, 21.6, 13.8; IR (KBr pellet) 1686 (C=O stretch), 1724 (C=O stretch), 3387 (NH stretch), 3430 (OH stretch); MS (CI/NH3) 373.

EXAMPLE 3

Preparation of N-(2-naphthyl)-2-hydroxy-2-methylpropionamide.

To a solution of 2-naphthol (533 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), eluting with 3:7 EtOAc/hexane to obtain N-(2-naphthyl)-2-hydroxy-2-methylpropionamide as a white solid (607 mg, 2.65 mmol, 71.6% yield).: mp 155–157° C. $^1$H NMR (300 MHz, DMSO) δ 9.74 (br s, 1H, N—H), 8.41 (d, 1H, $C_1$—H, J =2.20 Hz), 7.86–7.76(om's, 4H), 7.49–7.37 (om's, 2H), 5.80 (br s, 1H, O—H), 1.40 (s, 6H, $C(CH_3)_2$); $^{13}$C NMR (75 MHz, DMSO) δ 175.7, 136.2, 133.3, 129.8, 128.1, 127.4, 127.3, 126.3, 124.6, 120.6, 115.6, 72.5, 27.7; IR (KBr pellet) 1607, 1634, 1655 (amide C=O stretches), 3289 (NH/OH stretch); MS (CI/NH3) 247;

Analysis: Calculated C 73.34 H 6.59 N 6.11 Found C 72.97 H 6.57 N 5.89.

EXAMPLE 4

Preparation of N-(2-dibenzofuranyl)-2-hydroxy-2-methylpropionamide

To a solution of 2-hydroxydibenzofuran (682 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 18 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), eluting with 3:7 EtOAc/hexane to obtain N-(2- dibenzofuranyl)-2-hydroxy-2-methylpropionamide as an off-white solid (580 mg, 2.15 mmol, 58.1% yield). This was recrystallized from toluene for an analytical sample: mp 134–137° C. $^1$H NMR (300 MHz, CDCl$_3$) δ 8.83 (br s, 1H, N—H), 8.41 (d, 1H, C$_1$—H, J=2.34 Hz), 7.92 (m, 1H, Ar—H), 7.56–7.29 (om's, 5H, Ar—H), 2.46 (br s, 1H, O—H), 1.60 (s, 6H, C(CH$_3$)$_2$); $^{13}$C NMR (75 MHz, CDCl$_3$) δ 174.2, 156.8, 152.9, 132.8, 127.3, 124.6, 124.2, 122.7, 120.8, 119.5, 112.0, 111.7, 74.3, 28.0; IR (KBr pellet) 1651, 1668 (amide C═O stretches), 3364 (NH stretch), 3383 (OH stretch); MS (EI) 269; Analysis: Calculated C 71.36 H 5.61 N 5.20 Found C 71.43 H 5.58 N 5.06.

EXAMPLE 5

Preparation of 3-amino-1,3,5(10)-estratrien-17-ol and N-(3-amino-1,3,5,(10)-estratrien-17-ol-yl)-2-hydroxy-2-methylpropionamide To a solution of b-estradiol (1.00 g, 3.67 mmol) in dioxane (20 mL) was added NaH (Aldrich, dry, 400 mg, 16.7 mmol) and Cs$_2$CO$_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried (Na$_2$SO$_4$), and concentrated to about 3 g of material. The brown oil was chromatographed on silica (200 mL, 4 cm diam. column), eluting with 3:7 EtOAc/hexane to obtain first the starting estradiol (120 mg, 12% recovery) and then 3-amino-1,3,5 (10)-estratrien-17-ol as an off-white solid (100 mg, 0.368 mmol, 10% yield).: mp 75–77° C.; $^1$H NMR (300 MHz, DMSO) δ 6.90 (d, 1H, C$_1$—H, J=8.2 Hz), 6.33 (dd, 1H, C$_2$—H, J=8.2, 2.5 Hz), 6.25 (d, C$_4$—H, J=2.5 Hz), 4.70 (br s, 2H, NH$_2$), 4.47 (d, 1H, C$_{17}$—H, J=4.9 Hz), 3.55–3.47 (m, 1H), 2.68–2.62 (m, 2H, C$_6$—H), 2.23–1.72 (om's, 5H), 1.62–1.52 (m, 1H), 1.42–1.03 (om's, 7H), 0.66 (s, 3H, C$_{18}$—CH$_3$); $^{13}$C NMR (75 MHz, DMSO) δ 145.9, 136.2, 127.6, 125.5, 113.9, 111.9, 80.0, 49.5, 43.6, 42.8, 36.6, 29.9, 29.2, 27.1, 26.1, 22.8, 11.3; IR (KBr pellet) 3430 (NH/OH stretch); MS (EI) 271.

A column flush with EtOAc (700 ml) afforded the N-(3-amino-1,3,5,(10)-estratrien-17-ol-yl)-2-hydroxy-2-methylpropionamide as a brownish semi-solid (300 mg, 0.839 mmol, 22.8% yield). This was recrystallized from toluene to obtain an off-white powder: mp 175–177° C. $^1$H NMR (400 MHz, CDCl$_3$+few drops DMSO) δ 8.73 (br s, 1H, N—H), 7.35–7.15 (om's, 3H, Ar—H), 4.49 (br s, 1H, O—H), 3.65 (t, 1H, C$_{17}$—H, J=8.9 Hz), 2.81–2.76 (m, 2H, C$_6$—H), 2.34–1.78 (om's, 6H), 1.66–1.08 (om's, 8H), 1.44 (s, 6H, C(CH$_3$)$_2$), 0.71 (s, 3H, C$_{18}$—CH$_3$); $^{13}$C NMR (100 MHz, CDCl$_3$+few drops DMSO) δ 174.9, 137.2, 136.1, 135.2, 125.6, 119.6, 116.8, 81.4, 73.4, 49.9, 44.0, 43.0, 38.5, 36.6, 30.2, 29.5, 27.6, 27.0, 26.0, 22.9, 11.0; IR (KBr pellet) 1665 (C═O stretch), 3322 (NH stretch), 3376 (OH stretch); MS (EI) 357.

EXAMPLE 6

Preparation of N-(4-ethoxyphenyl)-2-hydroxy-2-methylpropionamide.

To a solution of 4-ethoxyphenol (511 mg, 3.70 mmol) in dioxane (20 mL) was added NaH (Aldrich, dry, 300 mg, 12.2 mmol) and Cs$_2$CO$_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried (Na$_2$SO$_4$), and concentrated to about 2 g of material. The brown oil was chromatographed on silica (200 mL, 4 cm diam. column), eluting with 3:7 EtOAc/hexane to obtain N-(4-ethoxyphenyl)-2-hydroxy-2-methylpropionamide as an off-white solid (536 mg, 2.40 mmol, 64.8% yield).: mp 146–148° C. $^1$H NMR (400 MHz, CDCl$_3$) δ 8.59 (br s, 1H, N—H), 7.45 (dd, 2H, Ar—H, J=9.0, 2.2 Hz), 6.84 (dd, 2H, Ar—H, J=9.0, 2.2 Hz), 4.00 (q, 2H, CH$_2$–CH$_3$, J=7.1 Hz), 2.73 (br s, 1H, O—H), 1.53 (s, 6H, C(CH$_3$)$_2$), 1.39 (t, 3H, CH$_2$–CH$_3$, J=7.1 Hz); $^{13}$C NMR (75 MHz, CDCl$_3$) δ 174.0, 155.7, 130.6, 74.0, 63.7, 27.9, 14.8; IR (KBr pellet) 1604, 1647 (amide C═O stretches), 3256 (NH stretch), 3281 (OH stretch); MS (CI/CH4) 224;

Analysis: Calculated C 64.55 H 7.67 N 6.27 Found C 64.16 H 7.47 N 6.07.

We claim:

1. A process of converting a hydroxy aromatic into a 2-hydroxy-N-arylacetamide without isolating a 2-aryloxyacetamide intermediate, comprising:

(1) treating a reaction mixture comprising a salt of a hydroxy aromatic with an alkylating agent; and (2) treating the reaction mixture with a Smiles solvent system and raising the temperature of the reaction mixture.

2. A process of converting a hydroxy aromatic into a 2-hydroxy-N-arylacetamide without isolating a 2-aryloxyacetamide intermediate, comprising:

(1) treating a reaction mixture comprising an alkylating solvent system and the a hydroxy aromatic to form a salt;

(2) treating the reaction mixture with an alkylating agent; and (3) treating the reaction mixture with a Smiles solvent system and raising the temperature of the reaction mixture.

3. The process according to claim 2, wherein the alkylating solvent system comprises a strong base, an ethereal solvent and a large alkaline metal cation.

4. The process according to claim 3, wherein the strong base comprises sodium hydride, potassium hydride lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium, or a mixture thereof.

5. The process according to claim 4, wherein the strong base comprises sodium hydride, potassium hydride, lithium hydride, or a mixture thereof.

6. The process according to claim 5, wherein the strong base comprises sodium hydride.

7. The process according to claim 3, wherein the ethereal solvent comprises 1,4-dioxane, 1,3-dioxane, tetrahydrofuran, dimethoxyethane, 2-methoxyethyl ether, propyl ether, isopropyl ether, n-butyl ether, sec-butyl ether, tert-butyl ether, n-butylmethyl ether, tert-butylmethyl ether, n-butylethyl ether, sec-butylethyl ether, tert-butylethyl ether, n-butylpropyl ether, sec-butylpropyl ether, tert-butylpropyl ether or a mixture thereof.

8. The process according to claim 7, wherein the ethereal solvent comprises 1,4-dioxane, 1,3-dioxane, tetrahydrofuran, dimethoxyethane or a mixture thereof.

9. The process according to claim 8, wherein the ethereal solvent comprises 1,4-dioxane, 1,3-dioxane or a mixture thereof.

10. The process according to claim 3, wherein the large alkaline metal cation comprises an inorganic cesium compound.

11. The process according to claim 10, wherein the inorganic cesium compound comprises cesium carbonate, cesium acetate, cesium bicarbonate, cesium bromide, cesium chloride, cesium fluoride, cesium iodide or a mixture thereof.

12. The process according to claim 11, wherein the inorganic cesium compound comprises cesium carbonate.

13. The process according to claim 2, wherein the alkylating agent comprises a secondary haloalkylamide, a tertiary haloalkylamide or a mixture thereof.

14. The process according to claim 12, wherein the alkylating agent comprises a tertiary haloalkylamide.

15. The process according to claim 14, wherein the tertiary haloalkylamide comprises 2-bromo-2-methylpropanamide, 2-bromo-2-ethylbutanamide or a mixture thereof.

16. The process according to claim 15, wherein the alkylating agent comprises 2-bromo-2-methylpropanamide.

17. The process according to claim 1, wherein the Smiles solvent system comprises an amide solvent, an anion-coordinating agent and a strong base.

18. The process according to claim 17, wherein the amide solvent comprises 1-methyl-2-pyrrolidinone, dimethylformamide, dimethylacetamide, or a mixture thereof.

19. The process according to claim 18, wherein the amide solvent comprises 1-methyl-2-pyrrolidinone.

20. The process according to claim 17, wherein the anion-coordinating agent comprises 1,3-dimethyltetrahydropyrimidin-2(1H)-one, hexamethylphosphoric triamide or a mixture thereof.

21. The process according to claim 20, wherein the anion-coordinating agent comprises 1,3-dimethyltetrahydropyrimidin-2(1H)-one.

22. The process according to claim 1, wherein the temperature of reaction mixture is between about 65° C. to about 250° C.

23. The process according to claim 22, wherein the reaction temperature is between about 125° C. to about 175° C.

24. The process according to claim 1, wherein (a) the salt of the hydroxy aromatic comprises an inorganic cesium compound; and (b) the Smiles solvent system comprises 1,3-dimethyltetrahydropyrimidin-2(1H)-one and 1-methyl-2-pyrrolidinone.

25. The process according to claim 1, wherein (a) the alkylating agent comprises 2-bromo-2-methylpropanamide; and (b) the Smiles solvent system comprises 1-methyl-2-pyrrolidinone, and 1,3-dimethyltetrahydropyrimidin-2(1H)-one.

26. The process according to claim 3, wherein the alkylating solvent system comprises (a) sodium hydride, (b) an ethereal solvent comprising 1,4-dioxane, 1,3-dioxane or a mixture thereof, and (c) an inorganic cesium compound.

27. An improved process of effecting an alkylation and Smiles rearrangment of a hydroxy aromatic to an 2-hydroxy-N-arylacetamide via a 2-aryloxyacetamide intermediate, wherein the improvement comprises not isolating the 2-aryloxyacetamide intermediate.

28. The process according to claim 27, wherein the 2-aryloxyacetamide intermediate is formed by the reaction of a salt of a hydroxy aromatic with an alkylating agent.

29. The process according to claim 28, wherein the 2-aryloxyacetamide intermediate is reacted with a Smiles solvent system.

30. The process according to claim 29, wherein the Smiles solvent system comprises a strong base, an ethereal solvent and a large alkaline metal cation.

31. The process according to claim 30, wherein the strong base comprises sodium hydride, potassium hydride, lithium hydride, lithium bis-trimethylsilyl amide, sodium bis-trimethylsilyl amide, potassium bis-trimethylsilyl amide, n-butyllithium, sec-butyllithium, iso-butyllithium , tert-butyllithium or a mixture thereof.

32. The process according to claim 30, wherein the ethereal solvent comprises 1,4-dioxane, 1,3-dioxane, tetrahydrofuran, dimethoxyethane, 2-methoxyethyl ether, propyl ether, isopropyl ether, n-butyl ether, sec-butyl ether, tert-butyl ether, n-butylmethyl ether, tert-butylmethyl ether, n-butylethyl ether, sec-butylethyl ether, tert-butylethyl ether, n-butylpropyl ether, sec-butylpropyl ether, tert-butylpropyl ether, or a mixture thereof.

\* \* \* \* \*